United States Patent [19]

Ezer et al.

[11] Patent Number: 4,624,959

[45] Date of Patent: Nov. 25, 1986

[54] N-{2-[(3-BENZOYL-2-PYRIDYL)-THIO]-ETHYL}-N'-CYANO-S-METHYL-ISOTHIOUREA, AND USE AS ANTI-ULCER AGENTS

[75] Inventors: Elemér Ezer; Kálmán Harsányi; Hajnalka Vikár née Pethő; Judit Matuz; László Szporny; Eszter Cholnoky; Csaba Kuthi; Ferenc Trischler; Béla Hegedüs; Márta Kápolnás née Pap; Anna Kállay née Sohonyai, all of Budapest, Hungary

[73] Assignee: Richter Gedeon Vegyeszeti Gyar Rt., Budapest, Hungary

[21] Appl. No.: 783,842

[22] Filed: Oct. 3, 1985

[30] Foreign Application Priority Data

Oct. 5, 1984 [HU] Hungary .............................. 3777/84

[51] Int. Cl.⁴ .......................................... C07D 213/78
[52] U.S. Cl. .................................... 514/346; 546/291

[58] Field of Search ................. 546/283, 291; 514/346

[56] References Cited

U.S. PATENT DOCUMENTS

4,000,285 12/1976 Parish .................................. 546/292

Primary Examiner—Henry R. Jiles
Assistant Examiner—J. Richter
Attorney, Agent, or Firm—Karl F. Ross; Herbert Dubno

[57] ABSTRACT

The compound N-{2-[(3-benzoyl-1-pyridyl)-thio]-ethyl}-N'-cyano-S-methyl-isothiourea and pharmaceutically acceptable acid addition salts thereof are disclosed as well as pharmaceutical compositions containing same and a method of treatment employing same. The compound or its acid addition salts are effective in treating gastric oedema and thus are useful in ulcer therapy.

4 Claims, No Drawings

N-{2-[(3-BENZOYL-2-PYRIDYL)-THIO]-ETHYL}-N'-CYANO-S-METHYL-ISOTHIOUREA, AND USE AS ANTI-ULCER AGENTS

The invention relates to new pyridine derivatives. More particularly, the invention concerns new pyridine derivatives of the formula (I),

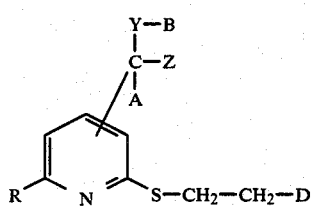 (I)

wherein

R is hydrogen or alkyl having from 1 to 4 carbon atoms,

Y is oxygen or sulfur, and

*if Y represents a sulfur atom,*

Z is phenyl optionally substituted by one or more halogen(s) and/or alkyl group(s) having from 1 to 4 carbon atoms, B stands for a —CH₂—CH₂—N(R¹,R²) group, in which R¹ and R² each independently stands for hydrogen, alkyl having from 1 to 4 carbon atoms or alkylphenyl having from 1 to 4 carbon atoms in the alkyl moiety, A is hydrogen; or

*if Y represents an oxygen atom,*

A and B together form a valency bond or separately stand for hydrogen,

Z is phenyl optionally substituted by one or more halogen(s) and/or alkyl group(s) having from 1 to 4 carbon atoms, hydroxyl or amino, with the *proviso* that if A and B separately represent hydrogen, Z is other than hydroxyl or amino, D is an —N(R³,R⁴) or —NH—E group, hydroxyl or halogen, wherein R³ and R⁴ each independently represents hydrogen, alkyl having from 1 to 4 carbon atoms or alkylphenyl having from 1 to 4 carbon atoms in the alkyl moiety, or an

group, in which R is as defined above, stands for a group of the formula (a), 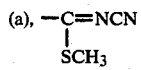 (a)

(b) 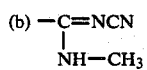 (b)

or (c), 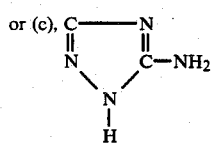 (c)

and the substituent

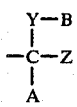

is attached to position 3- or 4- of the pyridine ring, with the *proviso* that if Y is oxygen and A and B together form a valency bond, D is other than an —N(R³,R⁴) group, and acid addition salts thereof.

According to another aspect of the invention there is provided a process for the preparation of the compounds of formula (I) by the following methods:

(a) to prepare compounds of the formula (IA),

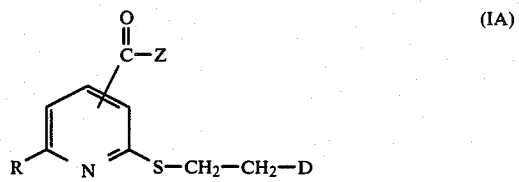 (IA)

in which R, Z and D are as defined above, (a₁) a 2-halopyridine derivative of the formula (II),

 (II)

wherein R and Z are as defined above,

X is halogen, is reacted with a thiol-derivative of the formula (III),

 HS—CH₂—CH₂—D (III)

wherein D is as defined above, or an acid addition salt thereof; or (a₂) a pyridine-2-thione derivative of the formula (IV),

 (IV)

wherein Z and R are as defined above, is reacted with a 2-haloethane derivative of the formula (V),

 X—CH₂—CH₂—D (V)

wherein D is as defined above, and

X is halogen, or an acid addition salt thereof, and, if desired, a compound of the formula (IA), in which Z is phenyl optionally substituted by one or more halogen(s) and/or alkyl group(s) having from 1 to 4 carbon atoms, R and D are as defined above, is reduced, optionally after deliberation from the salt thereof or after separation;

(b) to prepare compounds of the formula (IB'),

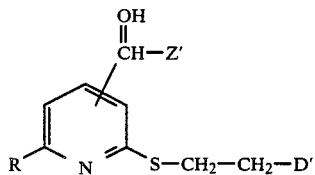
(IB')

wherein

Z' is phenyl optionally substituted by one or more halogen(s) and/or alkyl(s) having from 1 to 4 carbon atoms, D' is an —N(R³,R⁴) group, in which R³ and R⁴ are as defined above, reducing a compound of the formula (IA')

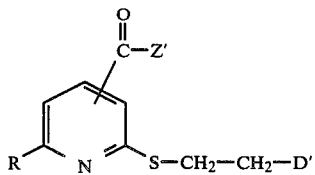
(IA')

wherein R, Z' and D' are as defined above; or (c) to prepare compounds of the formula (IC),

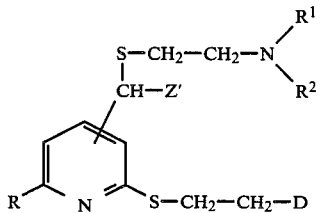
(IC)

wherein Z', R, D, R¹ and R² are as defined above, a compound of the formula (IB),

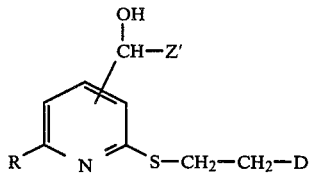
(IB)

wherein R, D and Z' are as defined above, is reacted with a compound of the formula (VI),

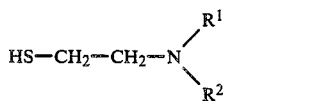
(VI)

wherein R¹ and R² are as defined above,
or an acid addition salt thereof, and, if desired, in a compound of the formula (I) obtained, in which R, A, B, Y, Z, R¹, R², R³, R⁴ and E are as defined above, a group D is converted into another group falling under the definition of D as given hereinabove, and/or, if desired, a compound of the formula (I) obtained is converted into an acid addition salt thereof or is deliberated therefrom.

Compounds of the formula (I) are partly pharmaceutically active, in particular show valuable anti-ulcer activity, partly are intermediates in the preparation of other, pharmaceutically active pyridine derivatives, e.g. disclosed in the commonly assigned copending application Ser. No. filed concurrently herewith and based upon Hungarian application No. 3775/84 filed Oct. 5, 1984 (attorney's docket No. 15431).

According to a still further aspect of the invention there are provided pharmaceutical compositions containing at least one compound of the formula (I) or an acid addition salt thereof in association with a pharmaceutical carrier and/or excipient.

In the above formulae in the definition of R, Z, R¹, R², R³ and R⁴ the term "alkyl having from 1 to 4 carbon atoms" is used to refer to straight-chained or branched alkyl groups, e.g. methyl, ethyl, n-propyl, isopropyl, n-butyl, isobutyl, sec.-butyl, tert.-butyl.

In the definition of R¹, R², R³ and R⁴ the alkyl-phenyl group having 1 to 4 carbon atoms in the alkyl moiety may contain as an alkyl part the above straight-chained or branched alkyl groups, and preferably is benzyl.

In the definition of Z the phenyl group is preferably unsubstituted or carries one or two substituents. Preferred substituents are chlorine and methyl.

X as a halogen atom is fluorine, chlorine, bromine or iodine, preferably chlorine or bromine.

Structurally related compounds are disclosed in the Japanese patent application No. 55-2920, published under No. 56-100765, most of which contain an alkyl- or dialkyl-aminoalkoxy side-chain in the 2-position. According to the Japanese patent application the compounds have antiapomorphine, muscle relaxant, tranquilizing and cerebral blood flow increasing activities, without any numerical pharmacological data. There is no disclosure which would suggest that the described compounds have anti-ulcer activity or may be used as intermediates in the preparation of other, pharmaceutically active compounds.

Pyridine-2-thiol derivatives are described in the Japanese patent specification No. 175,108. Certain representatives of the disclosed compounds, which are structurally significantly different from the compounds according to the present invention, can be employed for the phagocytosis of leucocytes and macrophages and for the treatment of rheumatoid arthritis.

According to process (a₁) of the invention the compounds of formula (II) are reacted with the compounds of formula (III), wherein the substituents are as hereinbefore defined, in a solvent, preferably in the presence of an acid binding agent. As a solvent preferably lower alcohols having from 1 to 4 carbon atoms, water or a mixture thereof may be employed. Preferred acid binding agents are the alkali metal hydroxides, carbonates, alcoholates, or organic bases, such as triethyl amine or quaternary ammonium compounds. The reaction temperature may vary within a wide range, depending on the solvent employed and on possible side-reactions. It is preferred, however, to carry out the reaction between 25° C. and 80° C. in order to achieve an acceptable reaction velocity. By proper selection of the solvent it can be achieved that after termination of the reaction the inorganic salts may be filtered off. After evaporation of the reaction mixture the crystalline products may be purified by recrystallization, and the products, which cannot be crystallized in base form can be isolated from their aqueous solutions by extraction with water-immiscible organic solvents, such as chlorinated hydrocarbons, ethers or ethyl acetate and evaporation of the organic phase. If desired, the product can further be purified by distillation in vacuum. The products having poor crystallization properties in base form can be converted into corresponding, readily crystallizable acid addition salts, preferably hydrochlorides.

Process ($a_1$) according to the invention can be performed in an acidic medium, too. In this case the reactants are reacted preferably in a concentrated aqueous hydrochloric acid solution, at the boiling point of the reaction mixture.

In process ($a_2$) the reaction of the compounds of formula (IV) with the compounds of formula (V) is carried out essentially as described in connection with process ($a_1$), first variant, in the presence of a base.

The reduction of the compounds of formula (IA), in which Z is a phenyl group optionally substituted by one or more halogen(s) and/or alkyl group(s) having from 1 to 4 carbon atoms into the corresponding compounds of formula (IB) and the reduction of the formula (IA') into the corresponding compounds of the formula (IB') (the substituents are as defined hereinabove), i.e. process (b) is carried out with a reducing agent suitable for converting carbonyl compounds into hydroxy compounds. Suitable reducing agents include e.g. metals or complex metal hydrides, such as sodium tetrahydroborate. In this case the reaction is accomplished in water, lower alcohols having from 1 to 4 carbon atoms or mixtures thereof. If the compounds of formula (IA) are obtained in the form of acid addition salts, the bases are first deliberated from their salts. The reaction is carried out at a temperature between 25° C. and 50° C., preferably 30° C. and 40° C. The hydroxy compounds obtained are generally precipitated upon dilution of the reaction mixture with water, and can be filtered off in a crystalline form. Otherwise, the compounds can be isolated by evaporation of the reaction mixture and subsequent extraction.

If the reduction yields a crystalline compound, more steps may be combined, for example the product obtained in process variant ($a_1$) or ($a_2$) may be subjected to the reduction directly, without isolation.

Process variant (c) is generally carried out in an aqueous hydrochloric acid solution, a protic or dipolar organic solvent, e.g. acetonitrile, at a temperature between 80° C. and 130° C., preferably at the boiling point of the reaction mixture. When the reaction is complete, the solvent is evaporated and the product obtained is generally crystallized from an organic solvent and, if desired, purified by recrystallization.

Compounds of the formula (II) used as starting material in process variant ($a_1$) are partly known, thus some of them are described in the European patent application No. 80010027.2 published under No. 0032516, or can easily be prepared by known chemical reactions [Org. Synth. Coll. Vo. 4, 88 (1963); Wolfenstein and Hartwich, Ber. 48, 2034 (1915)].

Compounds of the formula (III) used in process variant ($a_1$), compounds of the formula (V) used in process variant ($a_2$) and compounds of the formula (VI) used in process variant (c) (D, X, $R^1$ and $R^2$ are as defined above) are known, commercially available compounds or can easily be prepared from such substances.

The pyridine-2-thione derivatives of the formula (IV) are either known (Spanish patent specifications Nos. 506,366, 506,367 and 506,368) or can be prepared from known, commercially available compounds by known methods.

The starting compounds of the formula (IA') used in process variant (b) are disclosed in the commonly assigned copending application Ser. No. 783,875 filed 10-3-85 based upon Hungarian patent application 3775/84 and can be prepared by the process described therein.

Compounds of formula (IB) used as starting materials in process variant (c) can for example be prepared by the reduction step of process (a) according to the invention or by the reduction according to process variant (b).

As mentioned hereinabove, in the new compounds of the formula (I) the substituent D can be converted into other substituents falling under the definition of D.

For example compounds of the formula (I), in which D represents an —N($R^3R^4$) gruop, wherein $R^3$ and $R^4$ are both hydrogen, can be converted into the corresponding compounds of formula (I), in which $R^3$ and/or $R^4$ is an

group (R is as defined above) by acylation.

In turn, from the compounds of formula (I), in which $R^3$ and/or $R^4$ is an

group (R is as defined above), the acyl group can be eliminated in a known manner, by hydrolysis, to yield the corresponding primary amines.

Compounds of the formula (I) can be converted into their acid addition salts by reaction with suitable acids. Salt formation can be carried out, for example, in an inert organic solvent, such as a $C_{1-6}$ aliphatic alcohol, by dissolving the compound of the formula (I) in the solvent and adding the selected acid or a solution thereof formed with the same solvent to the first solution until it becomes acidic. Thereafter the acid addition salt separates and can be removed from the reaction mixture e.g. by filtration.

The anti-ulcer activity of the new compounds has been investigated by the following method:

Gastric necrosis induced by acidic ethanol
(cytoprotective activity)

Female RG-Wistar rats weighing 120 to 150 g each were fasted for 24 hours. Water was given ad libitum. The compounds to be tested were administered orally, 30 minutes prior to the oral administration of a mixture of 1 ml. of concentrated hydrochloric acid and 50 ml. of absolute ethanol in a dose of 0.5 ml./100 g. of body weight. One hour later the animals were killed by overdosing with ether. Stomachs were removed and opened along the major curvature. After cleaning the wet weight of the stomachs was determined, and the difference between the wet weight obtained and the wet weight of the stomachs of untreated (control) animals was calculated in order to determine the degree of gastric oedema. The stomachs were then dried and the gastric lesions were observed visually. Lengths of lesions were measured in millimeters (Derelanko and Long, Proc. Soc. Exp. Biol. and Med. 166,394/1981/) and the length of the average lesions per stomach was given. Degree of cytoprotection was expressed in % related to the control. The statistical evaluation of the results was carried out by the Student test.

The following results have been obtained:

| Test compound | Gastric oedema inhibition ED$_{50}$ (mg./kg. p.o.) | Haemorrhagie injury ED$_{50}$ (mg./kg. p.o.) |
|---|---|---|
| A | 40.0 | 50.0 |

A = N—{2-[(3-benzoyl-2-pyridyl)-thio]-ethyl}-N'—cyano-S—methyl-isothiourea

The active compounds of the formula (I) may be formulated for therapeutic purposes. The invention therefore relates also to pharmaceutical compositions comprising as active ingredient at least one compound of formula (I), in association with pharmaceutical carriers and/or excipients. Carriers conventional for this purpose and suitable for parenteral or enteral administration as well as other additives may be used. As carriers solid or liquid compounds, for example water, gelatine, lactose, starch, pectin, magnesium stearate, stearic acid, talc, vegetable oils, such as peanut oil, olive oil, etc. can be used. The compounds can be formulated as conventional pharmaceutical formulations, for example in a solid (globular and angular pills, dragées, e.g. hard gelatine capsules) or liquid (injectable oily or aqueous solutions or suspensions) form. The quantity of the solid carrier can be varied within wide ranges, but preferably is between 25 mg. and 1 g. The compositions optionally contain also conventional pharmaceutical additives, such as preserving agents, wetting agents, salts for adjusting the osmotic pressure, buffers, flavoring and odoring substances.

The compositions according to the invention are prepared by conventional techniques of pharmaceutical industry, e.g. in case of solid formulations by sieving, admixing, granulation and pressing of the components. The formulations may be subjected also to further treatments, e.g. sterilization.

The compounds of the formula (I) are according to the Chemical Abstracts nomenclature substituted methanones, methanols or acid amides, depending on the functional group serving as a basis for designation. for sake of simplicity in the following Examples the compounds are designated as pyridine derivatives on the basis of the pyridine ring which is present in all of them, but the designation corresponding to the Chemical Abstracts nomenclature is also indicated.

The invention will now be illustrated in more detail in the following Examples, which are given for illustration and not limitation of our invention.

EXAMPLE 1

2-[(2-Aminoethyl)-thio]-3-(α-hydroxybenzyl)-pyridine.2HCl
2-[(2-Aminoethyl)-thio]-α-phenyl-3-pyridine-methanol.2HCl 31.50 g. (0.107 moles) of 2-[2-aminoethyl)-thio]-3-benzoyl-pyridine hydrochloride are dissolved in 150 cm$^3$ of 50% aqueous ethanol, the pH is adjusted to 10 with an aqueous sodium hydroxide solution, and 3.96 g. (0.105 moles) of sodium tetrahydroborate are then added to the reaction mixture under stirring, taking care that the internal temperature should be between 35° C. and 40° C. The mixture is stirred for further 1.5 hours, and is subsequently diluted with 250 cm$^3$ of water. The precipitated crystalline substance is filtered off and recrystallized from isopropanol. 20.2 g. (63.0%) of 2-[(2-aminoethyl)-thio]-3-(α-hydroxybenzyl)-pyridine are obtained, melting at 118 to 120° C.

8.0 g. of the above base are converted into the corresponding acid addition salt with hydrochloric acid in isopropanol. After recrystallization from isopropanol 8.45 g. (82.5%) of 2-[(2-aminoethyl)-thio]-3-(α-hydroxy-benzyl)-pyridine.2HCl are obtained, melting at 173° to 175° C.

Analysis for $C_{14}H_{16}N_2OS.2HCl$ (333.30): Calculated: C%=50.46, H%=5.44, N%=8.41, S%=9.62; found: C%=50.30, H%=5.40, N%=8.34, S%=9.35.

IR spectrum (KBr): 3360, 3300 cm$^{-1}$ —NH$_2$; 3400-2100 cm$^{-1}$ —OH; 1590, 790, 765 cm$^{-1}$; 750, 722, 700 cm$^{-1}$—Ar.

NMR spectrum (CDCl$_3$+DMSOd$_6$): 2.9 ppm, t, —S—CH$_2$—; 3.3 ppm, m,

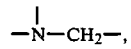

6.1 ppm, s,

7.0–8.0 ppm, m, pyridine 4,5-H and phenyl ring; 8.4 ppm, 2×d, pyridine 6-H.

EXAMPLE 2

2-{[2-(N,N-Dimethylamino)-ethyl]-thio}-3-(α-hydroxybenzyl)-pyridine
2-{[2-(N,N-Dimethylamino)-ethyl]-thio}-α-phenyl-3-pyridine methanol 13.2 g. (0.05 moles) of 2-[(2-aminoethyl)-thio]-3-(α-hydroxybenzyl)-pyridine, 11.3 cm$^3$ of 85% formic acid and 9.4 g. 35% formaline are boiled for 20 hours, whereupon 4.3 cm$^3$ of concentrated hydrochloric acid are added to the solution, which is then evaporated. The residue is dissolved in water, the pH is adjusted to 12 with a 10% aqueous sodium hydroxide solution, and the mixture is stirred for several hours. It is shaken with ethyl acetate, the solvent is eliminated, and the residue is crystallized from 25 cm$^3$ of acetonitrile. 11.22 g. (79.2%) of 2-{[2-(N,N-dimethylamino)-ethyl]-thio}-3-(α-hydroxybenzyl)-pyridine are obtained, melting at 88° to 89° C.

Analysis for $C_{16}H_{15}N_2OS$ (283.37): Calculated: N%=9.89, S%=11.33%; found: N%=9.93; S%=10.90%.

IR spectrum (KBr) 3300-2200 cm$^{-1}$ —OH; 2780 cm$^{-1}$ —N—CH$_3$; 1592, 797, 750, 709 cm$^{-1}$ —Ar.

NMR spectrum (CDCl$_3$) 2.2 ppm, s, —N—CH$_3$; 2.5 ppm, t, —S—CH$_2$—; 3.2 ppm, t, —N—CH$_2$—; 4.7 ppm, $^x$b, —O—H; 6.1 ppm, s,

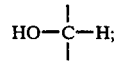

6.8–7.7 ppm, m, phenyl ring+pyridine 4,5H; 8.3 ppm, 2×d, pyridine 6-H.

EXAMPLE 3

2-[(2-Aminoethyl)-thio]-pyridine-3-carboxamide
2-[(2-Aminoethyl)-thio]-3-pyridine-carboxamide Into a hot solution of 7.83 g. (0.05 moles) of 2-chloronicotinic acid amide and 8.51 g. (0.075 moles) of cisteamine.HCl in 100 cm³ of ethanol, a solution of 8.4 g. (0.13 moles) of a 85% potassium hydroxide solution in 50 cm³ of ethanol is added in 30 minutes. The reaction mixture boiled for 30 minutes, the inorganic salt is filtered off and the solution is evaporated. The crystalline crude product is recrystallized from ethanol. 6.33 g. (64.2%) of 2-[(2-aminoethyl)-thio]-pyridine-3-carboxamide are obtained, melting at 131° to 133° C.

Analysis for $C_8H_{11}ON_3S$ (197.25): Calculated: C%=48.71, H%=5.62, N%=21.30, S%=16.25; found: C%=48.84, H%=5.41, N%=21.36, S%=16.02.

Ir spectrum (KBr) 3370, 3180 cm$^{-1}$ —NH$_2$; 1640 cm$^{-1}$ >C=O, 1620 cm$^{-1}$ amide —NH$_2$; 1572, 730 cm$^{-1}$ —Ar.

NMR spectrum (DMSOd$_6$) 2.1 ppm, $^x$s, —NH$_2$; 2.8 ppm, m, —S—CH$_2$; 3.2 ppm, m, —N—CH$_2$; 7.2 ppm, q, pyridine 5-H; 7.8 ppm, 2×d, pyridine 4-H, 8.6 ppm, 2×d, pyridine 6-H.

EXAMPLE 4

α,2-{bis-[(2-Aminoethyl)-thio]}-3-benzyl-pyridine.2HCl
α,2-bis-[(2-Aminoethyl)-thio]-3-phenylmethyl-pyridine.2HCl A mixture of 5.2 g. (0.02 moles) of 2-[(2-aminoethyl)-thio]-3-(α-hydroxybenzyl)-pyridine, 1.13 g. (0.02 moles) of cisteamine.HCl and 4.0 cm³ (4.72 g., 0.048 moles) of concentrated hydrochloric acid is boiled for three hours, and upon cooling the yellow oil obtained is triturated with isopropanol. The precipitated crystals are filtered off and recrystallized from a mixture of acetone and water. 7.15 g (72.6%) of α,2-bis-[(2-aminoethyl)-thio]-3-benzyl-pyridine.2HCl are obtained, melting at 259° to 261° C.

Analysis for $C_{16}H_{23}N_3S_2Cl_2$ (392.40): Calculated: C%=48.97, H%=5.90, N%=10.71, S%=16.34, Cl%=18.07; found: C%=48.71, H%=5.72, N%=10.48, S%=15.93, Cl%=17.97.

IR spectrum (KBr) 3300–2300 cm$^{-1}$

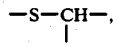

1275 cm$^{-1}$ —S—CH$_2$—; 1587, 788, 749, 693 cm$^{-1}$ —Ar.

NMR spectrum (DMSOd$_6$) 2.8–3.6 ppm, m, —S—CH$_2$— and

5.7 ppm, s,

7.6 ppm, m, phenyl ring+pyridine 5-H, 8.2 ppm, 2×d, pyridine 4-H, 8.7 ppm, 2×d, pyridine 6-H.

EXAMPLE 5

N-{2-[(3-Benzoyl-2-pyridyl)-thio]ethyl}-N'-cyano-S-methyl-isothiourea 4.42 g. (0.015 moles) of 2-[(2-aminoethyl)-thio]-3-benzoyl-pyridine.HCl are suspended in 10 cm³ of water, the base is deliberated by adding sodium carbonate, whereupon a solution of 2.35 g. (0.015 moles, 93.5%) of cyaniminodithiocarbonic acid dimethyl ester in 7.5 cm³ of ethanol is added and the reaction mixture is boiled for one hour. After cooling, the precipitated crystalline substance is filtered and recrystallized from acetonitrile. 4.05 g. (75.7%) of N-{2-[(3-benzoyl-2-pyridyl)-thio]-ethyl}-N'-cyano-S-methyl-isothiourea are obtained, melting at 180° to 181° C.

Analysis for $C_{17}H_{16}N_4OS_2$ (356.46): calculated: C%=57.28, H%=4.52, N%=15.72, S%=17.99; found: C%=57.32, H%=4.32, N%=15.87, S%=17.55.

IR spectrum (KBr) 3270 cm$^{-1}$

1633 cm$^{-1}$ >C=O, 1540 cm$^{-1}$ >C=N— 1593, 782, 753, 708 cm$^{-1}$ —Ar.

NMR spectrum (DMSOd$_6$) 2.5 ppm, s, —S—CH$_3$, 3.4 ppm, m, —S—CH$_2$ and

7.2 ppm, 2×d, pyridine 5-H, 7.5 ppm, m, phenyl ring, 7.7 ppm, 2×d, pyridine 4-H, 8.4 ppm, $^x$b,

8.6 ppm, 2×d, pyridine 6-H.

EXAMPLE 6

N'-{2-[(3-Benzoyl-2-pyridyl)-thio]-ethyl}-N-cyano-N"-methyl-guanidine 6.63 g. (0.051 moles) of N-cyano-N,S-dimethyl-isothiourea are dissolved in 100 ml of hot ethanol, a solution of 5.83 g. (0.051 moles) of cisteamine.HCl in 20 cm³ of water is added dropwise, followed by dropwise addition of 4.11 g. (0.103 moles) of sodium hydroxide in 16 cm³ of water, and the reaction mixture is boiled for one hour. Thereafter the solution of 11.18 g. (0.051 moles) of 3-benzoyl-2-chloro-pyridine in 10 cm³ of ethanol is added, and the mixture is boiled for 30 hours. After evaporation the residue is dissolved in dichloromethane and extracted with water. The dichloromethane phase is evaporated, the residue is triturated with isopropanol, filtered, dried and recrystallized from isopropanol. 9.3 g. (53.3%) of N'-{2-[(3-benzoyl-2-pyridyl)-thio]-ethyl}-N-cyano-N"-methyl-guanidine are obtained, melting at 132° to 133° C.

Analysis for C₁₇H₁₇N₅OS (339.42): Calculated: C%=60.16, H%=5.05, N%=20.63, S%=9.45; found: C%=60.17, H%=4.92, N%=20.76, S%=9.37.

IR spectrum (KBr): 3270 cm⁻¹ >NH, 2170 cm⁻¹ >C=N. 1654 cm⁻¹ >C=O, 1595 cm⁻¹ >C=N— 788, 750, 708 cm⁻¹ —Ar.

NMR spectrum (CDCl₃) 2.8 ppm, d→s, >N—CH₃ 3.3 ppm, m, —S—CH₂— and

6.6 ppm, ˣm, >NH 7.1 ppm, q, pyridine 5-H, 7.5 ppm, m, phenyl ring and pyridine 4-H, 8.5 ppm, 2×d, pyridine 6-H.

EXAMPLE 7

Phenyl-2-{[2-/(5-imino-1,2-dihydro-1,2,4-triazol-3-yl)-amino/-ethyl]-thio}-pyrid-3-yl-ketone
2-{[2-/(5-Imino-1,2-dihydro-1,2,4-triazol-3-yl)-amino/-ethyl]-thio}-3-pyridinyl-phenyl-methanone 5.5 g (0.015 moles) of N-{2-[(3-benzoyl-2-pyridyl)-thio]-ethyl}-N'-cyano-S-methyl-isothiourea are boiled with 16 cm³ (16.48 g., 0.33 moles) of hydrazine hydrate for one hour. The reaction mixture is then evaporated in vacuum, and the residue is recrystallized from aqueous dimethyl formamide. 2.8 g. (54.8%) of phenyl-2-{[(5-imino-1,2-dihydro-1,2,4-triazol-3-yl)-amino]-ethyl-thio}-pyrid-3-yl-ketone are obtained, melting at 230° to 232° C.

Analysis for C₁₆H₁₆N₆OS (340.40): Calculated: C%=56.45, H%=4.74, N%=24.69, O%=4.70, S%=9.62; found: C%=56.38, H%=4.59, N%=24.65, O%=4.82, S%=9.84.

IR spectrum (KBr): 3420, 3320, 3230, 3110 cm⁻¹ >NH, 1640 cm⁻¹ >C=O, 1570 cm⁻¹ >C=N—, 1602, 804, 751, 692 cm⁻¹—Ar.

NMR spectrum (CDCl₃) 3.3 ppm, b, —S—CH₂— and —N—CH₂—, 5.0–5.5 ppm, ˣb, >NH, 6.1 ppm, ˣs, —NH₂, 6.9–7.3 ppm, m, phenyl ring and pyridine 4,5-H, 8.3 ppm, 2xd, pyridine 6-H.

EXAMPLE 8

3-Benzoyl-2-[(2-hydroxyethyl)-thio]-pyridine.HCl {2-[(2-hydroxyethyl)-thio]-3-pyridinyl}-phenyl-methanone.HCl 10.88 g. (0.05 moles) of 3-benzoyl-2-chloropyridine and 3.84 g. (0.055 moles) of 2-mercapto-ethanol are dissolved in 30 cm³ of ethanol. To the solution a solution of 2.2 g. (0.055 moles) of sodium hydroxide in 30 cm³ of ethanol is added, and the reaction mixture is boiled for 2.5 hours. Thereafter 0.78 g. (0.01 mole) of 2-mercapto-ethanol is added to the mixture, which is boiled for further 1.5 hours. The inorganic salt is filtered off, the solution is evaporated, the residue is dissolved in water and extracted with 1,2-dichloroethane.

The organic phase is washed with 2 n sodium hydroxide and then with water, evaporated and converted into the corresponding hydrochloride with hydrochloric acid in ethyl acetate. The obtained 3-benzoyl-2-[(2-hydroxyethyl)-thio]-pyridine.HCl melts at 126° to 127° C.

Analysis for C₁₄H₁₃NO₂S.HCl (295.78): Calculated: C%=56.85, N%=4.74, S%=10.84, Cl%=11.99; Found: C%=56.68, N%=4.68, S%=10.53, Cl%=11.63.

IR Spectrum (KBr) 3360 cm⁻¹ —OH, 3100–2100 cm⁻¹

1600 cm⁻¹ C=O, 1600, 800, 758, 710 cm⁻¹ —Ar.

NMR spectrum (CDCl₃) 3.6 ppm, t, —S—CH₂—, 3.9 ppm, t, —O—CH₂—, 7.4–7.8 ppm, m, phenyl ring and pyridine 5-H, 8.0 ppm, 2×d, pyridine 4-H, 8.8 ppm, 2×d, pyridine 6-H, 9.5 ppm ˣs, —OH and

EXAMPLE 9

2-[(2-Aminoethyl)-thio]-4-(2,5-dimethyl-α-hydroxybenzyl)-6-propyl-pyridine.HCl
2-[(2-Aminoethyl)-thio]-α-(2,5-dimethylphenyl)-6-propyl-4-pyridine-methanol.HCl 28.78 g (0.10 moles) of 4-(2,5-dimethylbenzoyl)-2-chloro-6-propyl-pyridine and 17.04 g. (0.15 moles) of cisteamine.HCl are dissolved in 200 cm³ of ethanol, and to the hot solution a solution of 19.8 g. (0.3 moles) of 85% potassium hydroxide in 100 cm³ of ethanol is added dropwise. The suspension is boiled for 5.5 hours and subsequently is diluted with 500 cm³ of water. The solution is extracted with diisopropyl ether at pH 1, and with ethyl acetate at pH 12. The latter extract is washed with water and evaporated. The residue is dissolved in 60 cm³ of a 75% aqueous ethanol solution, whereupon 1.3 g. (0.035 moles) of sodium tetrahydroborate are added to the solution with stirring, taking case that the internal temperature should remain between 38° C. and 42° C. The mixture is stirred for further 2.5 hours, diluted with 150 cm³ of water, extracted with ether, and from the etheral solution of the base, after drying, the corresponding hydrochloride is prepared with hydrochloric acid in ether. The salt is filtered off and recrystallized from water. The obtained 2-[(2-aminoethyl)-thio]-4-(2,5-dimethyl-α-hydroxybenzyl)-6-propyl-pyridine.HCl melts at 69° to 72° C.

Analysis for C₁₉H₂₆N₂OS.HCl (366.95): Calculated: S%=8.74, Cl%=9.66; found: S%=8.90, Cl%=9.35.

IR spectrum (KBr) 3650–2200 cm⁻¹ —OH and

1632 cm⁻¹ —NH₂, 1050 cm⁻¹

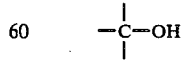

1585, 875, 803, 750 cm⁻¹ —Ar.

NMR spectrum (CDCl₃+DMSO d₆): 0.9 ppm, t, —CH₃, 1.7 ppm, q, —CH₂—CH₂—CH₃, 2.3 ppm, s, Ar—CH₃, 2.6 ppm, t, Ar—CH₂—CH₂— 3.4 ppm, b, —S—CH₂—CH₂—N, 5.8 ppm, s, CH—OH, 6.8–7.1 ppm, m, ArH.

EXAMPLE 10

2-[(2-Aminoethyl)-thio]-pyridine-3-carboxylic acid.HCl
2-[(2-Aminoethyl)-thio]-nicotinic acid.HCl 12.5 g. of cisteamine hydrochloride and 15.76 g. of 2-chloro-nicotinic acid are dissolved in 100 cm$^3$ of ethanol and the solution is brought up to the boil. 8.8 g. of solid sodium hydroxide are dissolved in 12 cm$^3$ of water, and the solution is added to the boiling solution dropwise, in half an hour. After two hours, the precipitated salt is filtered off while hot. The solution is then cooled and allowed to stand, and the precipitate is filtered off. The solution is evaporated, the residue is dissolved in water and the solution is acidified with a 2n aqueous hydrochloric acid solution. The precipitated unreacted 2-chloro-nicotinic acid is filtered off, and the aqueous acidic mother liquor is evaporated. The residue is recrystallized from a 50% aqueous ethanol and subsequently methanol solution, to yield 3.27 g. of 2-[(2-aminoethyl)-thio]-nicotinic acid hydrochloride melting at 240° to 243° C.

Analysis for C$_8$H$_{11}$ClN$_2$O$_2$S (234.72): Calculated: C%=40.93, H%=4.72; found: C%=41.20, H%=5.01.

IR spectrum (KBr): 3300-2100 cm$^{-1}$ OH, NH$_3^+$, 1704 cm$^{-1}$ C=O, 1590, 760, 702 cm$^{-1}$ Ar.

NMR spectrum (CDCl$_3$+DMSOd$_6$) 3.2 ppm, m, S—CH$_2$ and

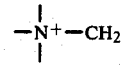

7.2, 8.2, 8.5 ppm, d pyridine ring H-S.

We claim:

1. N-{2-[(3-benzoyl-2-pyridyl)-thio]-ethyl}-N'-cyano-S-methyl-isothiourea or a pharmaceutically acceptable acid addition salt thereof.

2. A pharmaceutical composition for treating gastric oedema which comprises a therapeutically effective amount of the compound defined in claim 1 or a pharmaceutically acceptable acid addition salt thereof in association with a pharmaceutically acceptable inert carrier or diluent.

3. A method of treating gastric oedema in a mammal which comprises the step of administering to said mammal a therapeutically effective amount of the compound defined in claim 1 or a pharmaceutically acceptable acid addition salt thereof.

4. The method of treating gastic oedema in a mammal defined in claim 3 wherein the administration is oral administration.

* * * * *